United States Patent [19]

Shim

[11] 3,984,502
[45] Oct. 5, 1976

[54] METHOD OF PREPARING VINYL PHOSPHONATE ESTER OF PENTAERYTHRITOL

[75] Inventor: K. S. Shim, Irvington, N.Y.

[73] Assignee: Stauffer Chemical Company, Westport, Conn.

[22] Filed: Apr. 1, 1975

[21] Appl. No.: 564,923

Related U.S. Application Data

[63] Continuation of Ser. No. 460,398, April 12, 1974, abandoned.

[52] U.S. Cl. .................... 260/986; 260/969; 260/976; 260/977
[51] Int. Cl.² ........................................ C07F 9/40
[58] Field of Search ............ 260/927 R, 969, 976, 260/977, 986

[56] References Cited
UNITED STATES PATENTS

| | | | |
|---|---|---|---|
| 3,141,032 | 7/1964 | Friedman | 260/927 R |
| 3,382,301 | 5/1968 | Hechenbleikner et al. | 260/927 R X |
| 3,864,156 | 2/1975 | Weil | 117/136 |

FOREIGN PATENTS OR APPLICATIONS

| | | |
|---|---|---|
| 764,882 | 9/1971 | Belgium |
| 925,471 | 8/1972 | Italy |

OTHER PUBLICATIONS

Rubtsova et al., Chemical Abstracts, vol. 55 (1961), 25331f.

Rubtsova et al., Plasticheskie Massy, No. 3 (1961) pp. 13 to 14.

Primary Examiner—Richard L. Raymond
Attorney, Agent, or Firm—Richard P. Fennelly

[57] ABSTRACT

A vinyl phosphonate ester of pentaerythritol is provided corresponding to the following formula:

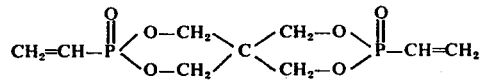

A process for its production is also disclosed. The compound is useful as a flame retardant, particularly for polyurethane foams, thermoplastic fibers and textiles.

9 Claims, No Drawings

METHOD OF PREPARING VINYL PHOSPHONATE ESTER OF PENTAERYTHRITOL

This is a continuation of application Ser. No. 460,398, filed Apr. 12, 1974, now abandoned.

BACKGROUND OF THE INVENTION

This invention relates to a vinyl phosphonate ester of pentaerythritol which is useful as a flame retardant.

Recently, there has been a great deal of interest in providing effective flame retardants for normally flammable substrates. For example, much interest is being shown in compounds which may be added to polyurethane foam to act as flame retardants without destroying the desirable physical characteristics of the foam. In addition, the flame retarding of flammable substrates such as textiles and thermoplastics, as well as polyurethane foam, for example, has become even more important as a result of recent governmental standards requiring that certain of these substrates be flame retarded.

In the past, however, the flame retarding of flammable substrates has presented some problems which have not been readily overcome. For example, one problem that arises results from the generally high processing temperatures (greater than 270°C.) required during the mixing and extruding of substrates such as thermoplastic fibers, like poly (ethylene terephthalate) commonly referred to as Dacron. These high processing temperatures can cause the volatilization or thermal degradation of the therein incorporated flame retardant.

Moreover, aside from severe processing conditions, flammable substrates such as polyurethane foam, are generally subjected to ambient conditions which alone are sufficient to cause the volatilization or thermal degradation of a therein incorporated flame retardant. In addition to the loss of flame retardant activity, this degradation of the flame retardant material within the foam substrate may also result in the loss of many of the desired physical characteristics of the foam.

Regarding the flame retardant compounds themselves, while it is generally recognized that compounds which contain, for example, bromine have improved flame retardant capabilities, many of these compounds are unacceptable because of their volatility and thermal instability.

On the other hand, prior art flame retardant compounds have been developed which, while possessing the requisite thermal stability do not possess sufficient flame retardant activity to allow for efficient use.

Accordingly, there is a need for flame retarding compounds, which while characterized by sufficient thermal stability, also possess efficient flame retardant capability.

TECHNICAL DISCLOSURE OF THE INVENTION

Therefore, it is one object of the present invention to provide a novel vinyl phosphonate ester of pentaerythritol which is useful as a flame retardant.

Another object of the present invention is to provide a vinyl phosphonate ester of pentaerythritol which is characterized by excellent thermal stability and excellent flame retardant activity.

Still another object of this invention is to provide a vinyl phosphonate ester of pentaerythritol which is particularly useful as a flame retardant for polyurethane foam, thermoplastic and thermoset resins, and textiles.

A further object of this invention is to provide a novel process for the preparation of the novel vinyl phosphonate ester of pentaerythritol of the present invention.

The novel vinyl phosphonate ester of pentaerythritol of the present invention is represented according to the following formula:

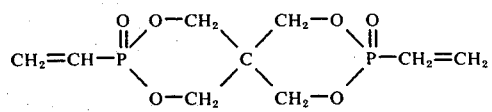

This compound is formed by the following preferred process:

The first step is the reaction of pentaerythritol, $C(CH_2OH)_4$, with phosphorus trichloride or phosphorus tribromide ($PX_3$, where X is Cl or Br) to form a product having the structure:

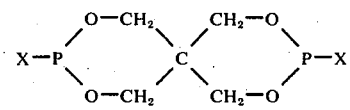

The reaction is carried out at a temperature of from 0° to 100°C, preferably at room temperature. A preferred molar range of $PX_3$ to the pentaerythritol is 4:1 to 1:1.

The second step is the reaction of the compound formed in step 1 with an equimolar amount of ethylene oxide in a suitable organic solvent, e.g. chloroform, or hexane, at a temperature of about 0°C to 100°C, preferably 0°–30°C, to form the following compound:

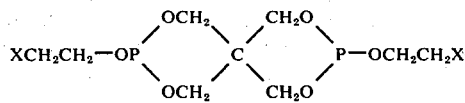

This compound is then treated to an Arbuzov rearrangement utilizing about 0.01% to 3%, by weight of the compound, of a suitable Arbuzov rearrangement catalyst, e.g. methyl iodide, at a temperature of above about 160°C, e.g. at 180°–190°C. Other Arbuzov rearrangement catalysts which can be used are the other $C_1$-$C_9$ alkyl halides, the aryl halides, e.g., benzyl bromide or iodide, the alkali metal halides and iodine. The compound that results has the following formula:

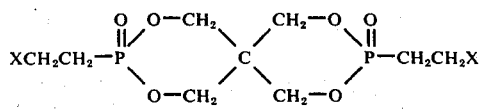

This compound can be converted into the novel vinyl ester of pentaerythritol by its dehydrohalogenation, preferably in the presence of an equimolar or slight excess of base, such as, sodium acetate or triethylamine, and a suitable solvent, e.g., tetrahydrofuran or 1, 2-dichlorobenzene, at a temperature of about 25°–60°C, preferably about 50°C.

As stated above, the vinyl phosphonate ester of pentaerythritol described herein is primarily intended for use as a flame retardant for such normally flammable substrates as thermoplastics, textiles, and for flexible or rigid polyurethane foams.

Illustrative of some thermoplastics which can be used with the novel flame retardant of this invention are polyesters, such as poly(ethylene terephthalate); cellulose esters, such as cellulose acetate and triacetate; cellulose ethers and other cellulosics such as rayon; polyamides, such as nylon; polyolefins such as polypropylene; polyethylene oxides, polypropylene oxides; acrylics and modacrylics, i.e., fibers based on acrylonitrile copolymers; saran fibers, i.e., fibers based on vinylidene chloride copolymers; spandex fibers, i.e., fibers based on a segmented polyurethane; vinyl fibers, i.e., fibers based on vinyl alcohol copolymers; vinyan fibers, i.e., fibers based on vinyl chloride copolymers and the like.

Of course, although the compounds of this invention are expecially well suited as flame retardants for thermoplastics and urethane foams, they also serve as efficient flame retardants in a wide variety of other flammable substrates such as paper, wood, polystyrene, polymethyl methacrylates, urethane coatings and elastomers and other natural and synthetic textiles such as cotton, wool, silk, sisal, jute, hemp, linen and the like.

The amount of vinyl phosphonate ester of pentaerythritol which is necessary to give satisfactory flame retardance in any particular flammable substrate system will generally vary over a wide range. Usually between about 1 to about 75%, based upon the weight of the substrate, of the flame retardant material is employed. Preferably between about 5% to about 15% is used. In general, any suitable known method of incorporating flame retardant materials may be utilized. For example, where thermoplastic fibers are the desired substrate, the flame retardants of the present invention may be blended with the molten polymers and extruded therewith to form the fibers. On the other hand, the flame retardant materials of this invention may be blended with the monomers prior to formation of the polymeric fiber material.

In addition, the flame retardants of the present invention may be added to textiles according to conventional procedures such as via aqueous or organic solutions which are either sprayed onto the textile or "padded on" by passing the textile through the solution while the latter is being held in a tank or other suitable container.

As also indicated above, the novel vinyl phosphonate flame retardant of this invention may also be incorporated in polyurethane foams. These polyurethane foams are well known in the art and are produced by the reaction of a di- or polyisocyanate and a di - or polyhydroxy (polyol) compound in the presence of a blowing agent and a catalyst. The foams can be made by any of the basic techniques used in foam formation, i.e., the prepolymer technique, the semi-prepolymer technique or the one-shot process. These techniques are well known and are described in the polyurethane art.

Having generally described the invention, the following example is given for the purposes of illustration:

EXAMPLE I

In a 2 liter flask containing 475g (3.5 moles) of pentaerythritol was added dropwise 1650g of phosphorus trichloride (12 moles) while stirring vigorously at room temperature. After this addition the mixture was heated for 4 hours at 65°C to complete the reaction and the excess PCl₃ was stripped at 65°C under aspirator pressure to give a white crystalline solid.

To the above mixture was then added chloroform (500ml), and ethylene oxide was introduced through a gas dispersing tube while the pot temperature was maintained at below 30°C using an icewater bath. The reaction was quite exothermic. Addition of ethylene oxide was continued until no free hydrogen chloride was generated from the mixture by the addition of a small amount of water.

The mixture was agitated overnight to complete the reaction. The solvent and excess ethylene oxide was stripped on a rotary evaporator to give 813g of light yellow liquid. Analysis showed a phosphorus content of 15.7% (theory, 17.6%) and a chlorine content of 28.3% (theory, 20.1%). The IR showed no hydroxyl peak.

In a 500 ml flask was placed 200 g of the product from the previous step and 2 drops of iodomethane. The reaction mixture was heated to 180°C over a period of 5 hours. To the mixture was then added 200 ml chloroform solvent and it was washed with aqueous saturated sodium carbonate solution and was dried over anhydrous magnesium sulfate. Removal of solvent was accomplished on a rotary evaporator and 140g of a colorless liquid. Analysis showed that the product had a phophorus content of 16.1% (theory, 17.6%) and a chlorine content of 22.5% (theory, 20.1%).

In a 250ml flask containing 50g of the compound and 50g tetrahydrofuran was added 50g triethylamine and the mixture was heated at 50°C for an hour. Upon cooling, the reaction mixture, the amine hydrochloride was separated as a cryatalline solid and was removed by filtration. The solvent was stripped on a rotary evaporator to give as the desired and product a colorless viscous liquid.

What is claimed is:

1. A process for forming a compound having the formula:

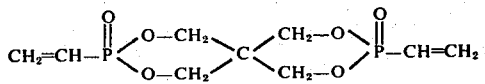

which comprises:

a. reacting pentaerythritol with a compound selected from the group consisting of phosphorus trichloride and phosphorus tribromide to form a product having the structure:

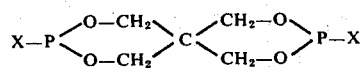

where X is selected from the group consisting of chlorine and bromine;

b. reacting the product from step (a) with ethylene oxide to form a compound having the structure:

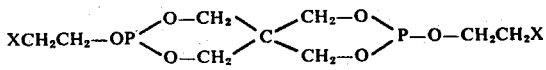

c. reacting the product from step (b) with an Arbuzov rearrangement catalyst to form an Arbuzov rearrangement product having the formula:

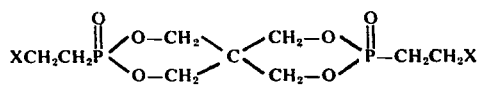

where X is as defined above; and d. dehydrohalogenating the product from step (c).

2. A process as claimed in claim 1 wherein the reaction in step (a) is carried out at a temperature of about 0°C to 100°C.

3. A process as claimed in claim 1 wherein the reaction in step (b) is carried out at a temperature of about 0°C to 100°C.

4. A process as claimed in claim 1 wherein the reaction in step (c) is carried out at a temperature of above about 160°C.

5. A process as claimed in claim 1 wherein the Arbuzov rearrangement catalyst is selected from the group consisting of the $C_1$-$C_9$ alkyl halides, the aryl halides, the alkali metal halides and iodine.

6. A process as claimed in claim 1 wherein about 0.01% to 3% of Arbuzov rearrangement catalyst is used.

7. A process as claimed in claim 1 wherein the dehydrohalogenation is carried out at a temperature of about 25°C to 60°C.

8. A process as claimed in claim 1 wherein the dehydrohalogenation is accomplished by using a base.

9. A process as claimed in claim 8 wherein the base is selected from the group consisting of sodium acetate and triethylamine.

* * * * *